US007580742B2

(12) United States Patent
Tan et al.

(10) Patent No.: US 7,580,742 B2
(45) Date of Patent: Aug. 25, 2009

(54) USING ELECTROENCEPHALOGRAPH SIGNALS FOR TASK CLASSIFICATION AND ACTIVITY RECOGNITION

(75) Inventors: Desney S Tan, Kirkland, WA (US); Johnny C Lee, Pittsburgh, PA (US)

(73) Assignee: Microsoft Corporation, Redmond, WA (US)

( * ) Notice: Subject to any disclaimer, the term of this patent is extended or adjusted under 35 U.S.C. 154(b) by 495 days.

(21) Appl. No.: 11/349,859

(22) Filed: Feb. 7, 2006

(65) Prior Publication Data

US 2007/0185697 A1    Aug. 9, 2007

(51) Int. Cl.
  *A61B 5/04*    (2006.01)
(52) U.S. Cl. ..................................... 600/544
(58) Field of Classification Search ................. 600/544, 600/545; 128/920–925
See application file for complete search history.

(56) References Cited

U.S. PATENT DOCUMENTS

| | | | | |
|---|---|---|---|---|
| 5,047,930 | A * | 9/1991 | Martens et al. | 600/301 |
| 6,067,467 | A * | 5/2000 | John | 600/544 |
| 6,317,627 | B1 * | 11/2001 | Ennen et al. | 600/544 |
| 6,496,724 | B1 * | 12/2002 | Levendowski et al. | 600/544 |
| 6,625,485 | B2 * | 9/2003 | Levendowski et al. | 600/544 |
| 2002/0082513 | A1 * | 6/2002 | Ennen et al. | 600/544 |
| 2002/0183644 | A1 * | 12/2002 | Levendowski et al. | 600/544 |
| 2006/0111644 | A1 * | 5/2006 | Guttag et al. | 600/544 |

OTHER PUBLICATIONS

Anderson, C.W., and Z. Sijerčić, "Classification of EEG Signals From Four Subjects During Five Mental Tasks," Dept. of Computer Science, Colorado State University, 1996.
"BrainMaster Technologies Home," *BrainMaster Technologies, Inc.*, n.d., <http://www.brainmaster.com/index.html> [retrieved Apr. 28, 2006].
Chen, D., and R. Vertegaal, "Using Mental Load for Managing Interruptions in Physiologically Attentive User Interfaces," *Proceedings of CHI 2004*, Vienna, Austria, Apr. 24-29, 2004, pp. 1513-1516.
Coyle, S., et al., "Brain-Computer Interfaces: A Review," *Interdisciplinary Science Reviews* 28(2):112-118, 2003.
Fayyad, U.M., and K.B. Irani, "On the Handling of Continuous-Valued Attributes in Decision Tree Generation," *Machine Learning* 8:87-102, 1992.

(Continued)

*Primary Examiner*—Charles A Marmor, II
*Assistant Examiner*—Navin Natnithithadha
(74) *Attorney, Agent, or Firm*—Lee & Hayes, PLLC (57) ABSTRACT

A method for classifying brain states in electroencephalograph (EEG) signals comprising building a classifier model and classifying brain states using the classifier model is described. Brain states are determined. Labeled EEG data is collected and divided into overlapping time windows. The time dimension is removed from each time window. Features are generated by computing the base features; combining the base features to form a larger feature set; pruning the large feature set; and further pruning the feature set for a particular machine learning technique. Brain states in unlabeled EEG data are classified using the classifier model by dividing the unlabeled EEG data into overlapping time windows and removing the time dimension from each time window. Features required by the classifier model are generated. Artifacts in the labeled and unlabeled EEG data comprise cognitive artifacts and non-cognitive artifacts.

16 Claims, 9 Drawing Sheets

OTHER PUBLICATIONS

Fisch, B.J., "*Fisch & Spehlmann's EEG Primer: Basic Principles of Digital and Analog EEG*," Elsevier, Amsterdam, 1999.

Fitzgibbon, S.P., et al., "Cognitive Tasks Augment Gamma EEG Power," *Clinical Neurophysiology 115*:1802-1809, 2004.

Fogarty, J., et al., "Examining Task Engagement in Sensor-Based Statistical Models of Human Interruptibility," *Proceedings of CHI 2005*, Portland, Oregon, Apr. 2-7, 2005, pp. 331-340.

Gevins, A., et al., "Towards Measurement of Brain Function in Operational Environments," *Biological Psychology 40*:169-186, 1995.

Gevins, A.S., et al., "EEG Patterns During 'Cognitive' Tasks. I. Methodology and Analysis of Complex Behaviors," *Electroencephalography Clinical Neurophysiology 47*:693-703, 1979.

Gevins, A.S., et al., "EEG Patterns During 'Cognitive' Tasks. II. Analysis of Controlled Tasks," *Electroencephalography Clinical Neurrophysiology* 47:704-710, 1979.

Keirn, A.A., and J.I. Aunon, "A New Mode of Communication Between Man and His Surroundings," *IEEE Transactions on Biomedical Engineering 37*(12):1209-1214, Dec. 1990.

Kitamura, Y., et al., "Things Happening in the Brain While Humans Learn to Use New Tools," *Proceedings of CHI 2003*, Ft. Lauderdale, Florida, Apr. 5-10, 2003, *CHI 5*(1):417-424.

Kramer, A.F., "Physiological Metrics of Mental Workload: A Review of Recent Progress," in Diane L. Damos (ed.), *Multiple-Task Performance*, Taylor & Francis Ltd., London, 1991, pp. 280-328.

Mason, S.G., and G.E. Birch, "A General Framework for Brain-Computer Interface Design," *IEEE Transactions on Neural Systems and Rehabilitation Engineering 11*(1):70-85, Mar. 2003.

Millán, J. del R., "Adaptive Brain Interfaces," *Communications of the ACM 46*(3):75-80, Mar. 2003.

OpenEEG Project, n.d., <http://openeeg.sourceforge.net> [retrieved Apr. 28, 2006].

Palaniappan, R., "Brain Computer Interface Design Using Band Powers Extracted During Mental Tasks," *Proceedings of the 2nd International EMBS Conference on Neural Engineering IEEE 2*, Arlington, Virginia, Mar. 16-19, 2005, pp. 321-324.

Picton, T.W., et al., "Guidelines for Using Human Event-Related Potentials to Study Cognition: Recording Standards and Publication Criteria," *Psychophysiology 37*:127-152, 2000.

Smith, R.C., "Electroencephalograph Based Brain Computer Interfaces," master's thesis, University College Dublin, Ireland, Feb. 2004.

Velichkovsky, B.M., and J.P. Hansen, "New Technological Windows Into Mind: There Is More in Eyes and Brains for Human-Computer Interaction," *Proceedings of CHI 96*, Vancouver, British Columbia, Canada, Apr. 13-18, 1996, pp. 496-503.

van Boxtel, G.J.M., "Computational and Statistical Methods for Analyzing Event-Related Potential Data," *Behavior Research Methods, Instruments & Computers 30*(1):87-102, 1998.

Witten, I.H., and E. Frank, "*Data Mining: Practical Machine Learning Tools and Techniques*," 2d ed., Morgan Kaufmann, San Francisco, 2005.

Wolpaw, J.R., et al., "Brain-Computer Interfaces for Communication and Control," *Clinical Neurophysiology 113*:767-791, 2002.

\* cited by examiner

USING ELECTROENCEPHALOGRAPH SIGNALS FOR TASK CLASSIFICATION AND ACTIVITY RECOGNITION

BACKGROUND

When studying how humans interact with computing devices, it is desirable to be able to determine the effectiveness of a computer-user interface, i.e., a user interface. A traditional way of determining the effectiveness of a user interface is to present a computer user, i.e., a user, with a task, observe the user as he or she operates the user interface to complete the task, and ask the user questions before, during, and/or after the task is performed. The observed behavior and answers to the questions are characterized and quantified. The quantified results are analyzed to determine the effectiveness of the user interface.

Cognitive neuroscience techniques can be used to provide a more direct way to determine the effectiveness of user interfaces. A typical cognitive neuroscience technique involves attaching electrical sensors, i.e., sensors, to various points on a user's scalp. The sensors are then connected to an electroencephalograph (EEG). One use of an EEG is to sense electrical changes within the brain that correspond to certain brain states. It is possible to determine the effectiveness of a user interface by analyzing a user's brain states before, during, and/or after a user performs a task using the user interface.

As the name implies "cognitive" neuroscience techniques, also called cognitive techniques, are focused on thought processes. Cognitive techniques analyze electrical signals caused by electrical changes within the brain, i.e., EEG signals. The EEG signals contain data and patterns of data associated with brain states, which can be used to infer the existence of thought processes. A problem with cognitive techniques is that EEG signals often contain artifacts, i.e., unwanted data, that may distort the brain state information. In the past, attempts have been made to overcome artifacts or "noise problems" by filtering EEG signals and by using neurofeedback. While effective at eliminating some artifacts, filtering and neurofeedback add significant cost and complexity to cognitive techniques which in turn reduces the utility of applying cognitive techniques to determine the effectiveness of user interfaces.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for classifying brain states using EEG signals is disclosed. The method is capable of determining the persistence of brain states and the transitions between brain states. The method comprises building a classifier model using labeled EEG data and classifying brain states in unlabeled EEG data using the classifier model.

An exemplary classifier model is built by determining brain states; collecting a set of labeled EEG data; and dividing the set into overlapping time windows. The time dimension is removed from each time window, features of the data, i.e., features, are generated for the time windows, and the classifier model is built. Features are generated from the time windows of the labeled EEG data by computing the base features of the time windows; combining the base features to form a larger feature set; pruning the larger feature set without regard to machine learning techniques; and further pruning the feature set for a particular machine learning technique. Brain states are classified using the classifier model by collecting a set of unlabeled EEG data, dividing the unlabeled EEG data into overlapping time windows, and removing the time dimension from each time window. Features required by the classifier model are generated from the time windows. The classifier model is used to classify brain states in the unlabeled EEG data. The size of averaging kernels is chosen and the classifier output is averaged over adjacent time windows. The labeled and unlabeled EEG data contains both brain state data and artifacts.

In one exemplary application, the EEG signals are collected from sensors attached to the scalps of neurologically healthy individuals ("users") as the users operate user interfaces. Preferably, the number of sensors is substantially less than the number of sensors normally employed in EEG signal data collection—four (4) sensors forming two sensor pairs, for example. Preferably, the brain states are associated with at least one condition chosen from the group of user conditions comprising: interruptability, cognitive workload, task engagement, communication mediation, interpreting and predicting system response, surprise, satisfaction, and frustration.

Exemplary uses of the method include, but are not limited to: comparing the cognitive workload levels or workload types of a plurality of user interfaces; evaluating cognitive utility of user interfaces in real time to enable dynamically adapting user interfaces to users' states; and presenting an enhanced, detailed awareness of the cognitive workload of groups of users.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Computing devices often provide user interfaces that enable users to interact with the computing devices. An exemplary user interface comprises an input device, an output device, and a computer software program that enables a user to control the computing device and output device by using the input device. Exemplary input devices include, but are not limited to, keyboards, keypads, optical and mechanical mice, touchpads, electronic and optical pens, electronic gloves, electronic wands, etc. Exemplary output devices include, but are not limited to, electronic displays, such as liquid crystal displays (LCDs), plasma screens, cathode ray tubes (CRTs), digital image projectors, etc.; and electromechanical devices, such as force feedback mechanisms, steering mechanisms for vehicles, controls for industrial machinery, robotic appendages, robots, etc.

An important part of the process of developing a user interface is evaluating the effectiveness of the user interface. Traditionally, the effectiveness of a user interface is determined by observing users as they operate the user interface to perform prescribed tasks. Often, users answer questions before, during, and/or after the tasks are performed. The questions may be about the user interface, the task, the user's perceptions, etc. Observations about the users' behaviors and answers to the questions are characterized and quantified. The quantified results are analyzed to determine the effectiveness of the user interface.

There are problems with evaluating a user interface in the manner described above. Asking a user questions after a task is performed may result in losing information because the user is likely to forget details about the task and his or her reactions to a user interface. An alternative approach, asking a user questions while the user is performing a task, is likely to distract the user from the task and the user interface. In either approach, the verbal information a user provides may not be accurate. Those skilled in the art appreciate that human beings are often poor reporters of their own actions. Relying solely on observing a user's external actions is not likely to provide enough information about what a user is thinking or feeling while operating a user interface. It is possible that user actions may be misinterpreted or missed by an observer.

Less interruptive and more informative techniques of determining user interface effectiveness are possible using EEGs. An EEG measures and records the differences in voltage levels between two sensors, i.e., a sensor pair, in a sensor array comprising one or more sensor pairs, preferably over time. Electrical changes within the brain of a user cause changes in the voltage level between the two sensors comprising a sensor pair. The voltage levels from the sensor pairs in the sensor array are passed to the EEG where the voltage levels are recorded for further processing and analysis. EEGs provide a passive, non-invasive way to study brain activity. Compared to other brain activity analysis tools, EEGs provide a relatively coarse representation of brain activity. However, EEGs require only a small amount of operator training and are safe when used repeatedly or used for extended periods of time.

Techniques for analyzing EEG signals may focus on neurological phenomena or on the general data features of EEG signals. Analysis techniques that focus on neurological phenomena require that the neurological phenomena be tightly correlated with specific patterns in an EEG signal, i.e., signal patterns. There are various neurological responses known to be associated with specific signal patterns. For example, the P300 is a well-known signal pattern and is often referred to as the "surprise" signal pattern. The P300 signal pattern appears about 300 milliseconds after a user responds to an event the user did not expect or responds to an unfamiliar stimulus, i.e., a surprise response. The P300 signal pattern is often used for lie detection. Analyzing occurrences of the P300 signal pattern in an EEG signal allows a skilled lie detector operator to determine if a person is lying.

Analysis techniques that focus on general data features of the EEG signal extract the data contained in the EEG signals and pass the data to machine learning algorithms. Focusing on general data features of the EEG signal allows the machine learning algorithms to treat the brain as a black box in that no information about the brain or the user goes into the analysis. The analysis usually involves signal processing and may also involve data feature generation, i.e., feature generation, and selection of relevant data features, i.e., features. Machine learning techniques are used to classify the results. Machine learning techniques acquire knowledge automatically from examples, i.e., from source data as opposed to performance systems, which acquire knowledge from human experts. Machine learning techniques enable systems, e.g., computing devices, to autonomously acquire and integrate knowledge, i.e., learn- from experience, analytical observation, etc., resulting in systems that can continuously self-improve and thereby offer increased efficiency and effectiveness. Machine learning techniques include, but are not limited to, Bayesian networks, neural networks, decision trees, symbolic learning, genetic algorithms, and support vector machines (SVMs).

In order for the traditional EEG signal analysis processes described above to operate correctly, a plurality of sensors, e.g., eight sensor pair for a total of 16 sensors, are placed on the user's scalp in a specific, standard, predetermined pattern and artifacts are filtered out of the signals from the sensors. It is also helpful to reduce user movement because physical movement causes artifacts. User movement may be reduced by having the users sit still and focus on one point or close their eyes. Physical restraints may be used to restrict the movement of users' heads and/or limbs.

Cognitive techniques using the traditional EEG signal analysis processes described above rely on sensing and analyzing electrical signals caused by electrical changes within the brain. Certain patterns in electrical signals generated by the brain may be associated with brain activities and brain states that may then be used to infer the existence of thought processes, e.g., the surprise signal pattern to infer surprise. The electrical signal patterns recorded by the EEG can be classified as representing cognitive or non-cognitive activities. Examples of cognitive activities are arithmetic calculations, imagining scenes or images, recalling songs, and so on. A cognitive activity generates one or more cognitive signals and artifacts, i.e., cognitive artifacts. Examples of non-cognitive activities are moving a computer mouse and typing on a keyboard. More subtle examples of non-cognitive activities are eye blinking, eye movement, and twitching. A non-cognitive activity generates one or more non-cognitive signal and artifacts, i.e., non-cognitive artifacts.

Often the strength and/or number of the artifacts is great enough to overwhelm the cognitive and non-cognitive data in the signals making it difficult or impossible to recognize signal patterns. The problem of artifacts overwhelming signal patterns may be overcome by filtering. If a signal can be sufficiently characterized, a filter may be constructed to allow the signal to pass through the EEG while artifacts are blocked. Conversely, if an artifact is well-known, a filter may be constructed to block the well-known artifact.

Another solution to the problem of artifacts overwhelming signal patterns is to increase the strength and clarity of signal patterns. To ensure that clear, strong signal patterns are generated, users may be given neurofeedback training. In neurofeedback training a mechanism, such as a display connected to an EEG, provides the user with information, i.e., feedback, that helps the user determine how well he or she is performing a particular task. As the user uses the feedback to improve performance of the task, the signal patterns associated with the task are strengthened. An exemplary task is moving a cursor on a display in a user interface. Normally, the cursor may be moved using a mouse, a touchpad, or the like. A user may, through the use of neurofeedback, learn how to "think about moving the cursor" in order to move a cursor in a particular direction, e.g., left. The user makes an attempt to "think about" moving the cursor to the left. The user generates certain signal patterns that are sensed by a sensor array and passed to an EEG. The EEG processes the signals, recognizes the signal patterns, and moves the cursor in accord with the signal patterns providing the user with immediate feedback. If the cursor has moved left, the user knows that the brain state achieved is the appropriate brain state for moving the cursor to the left. If the cursor does not move or moves in the wrong direction, e.g. to the right, the user must make an attempt to achieve a different brain state. As the user learns to move the cursor, the signal pattern associated with the brain state for moving the cursor is strengthened so that artifacts do not overwhelm the signal pattern.

Two traditional cognitive neuroscience techniques that may be used to provide neurofeedback are operant conditioning and pattern recognition. In operant conditioning, the analysis system, i.e., system, has various defined brain states, e.g., a brain state in which a user solves a math problem versus a brain state in which a user thinks about moving her left arm. For example, a user is told that she will be doing two tasks, solving a math problem or thinking about moving her left arm and is also told that the system will be able to tell which task is being performed. The user performs a task, e.g., thinks about moving her left arm, and observes output on the system's display. If the output does not match a standard, the user tries again and augments whatever she was doing. Thus, the user is trained to optimally perform the appropriate mental task.

In pattern recognition, the system recognizes patterns in the EEG signals from the sensors attached a user. Initially, the user is not assigned a task. Instead, the user is asked to think about anything as long as whatever the user thinks about generates a stable, recognizable, and reproducible brain state. The nature of the brain state is not important and what the user does to achieve the brain state is not important as long as the user can reliably reproduce the brain state. The system records the signal pattern in the EEG signal present during the stable, recognizable, and reproducible brain state. Thereafter, when a user reproduces the brain state and the system recognizes the signal pattern associated with the brain state, the system executes a task, e.g., moving a cursor to the left.

While filtering artifacts, using neurofeedback to strengthen signals, using a plurality of specifically placed sensors, and restricting users' movements may help solve the problem of artifacts overwhelming signal patterns, such strategies restrict the application of cognitive neuroscience techniques for assessing user interface effectiveness. Filtering artifacts reduces the amount of computer resources that can be dedicated to assessing user interface effectiveness. Neurofeedback requires time and effort to train users to perform specific tasks in specific ways. Having to apply many sensors in predetermined positions requires researchers that are trained in such application and consumes time and money. Using many sensors and restricting users movements makes it less likely that suitable subjects, i.e., users, may be willing to participate in studies, and makes the system less useful for evaluating real interfaces in real world scenarios.

An exemplary method for assessing user interface effectiveness that avoids the problems described above by using cognitive and non-cognitive artifacts, instead of filtering out artifacts, is described below. The method is not focused on using the brain to control parts of a system but is instead focused on using information derived from cognitive and non-cognitive artifacts to determine how well a user interface works. The method is fairly general in that factors of interest may be prespecified. The method may be used to evaluate the performance of users or to evaluate the performance of a user interface. A user's performance can be evaluated by comparing how hard a user works on one task compared to another task. A user interface's performance can be evaluated by comparing how hard users work on one user interface versus another user interface.

Embodiments of the method may be understood as a combination of operant conditioning and pattern recognition, described above. In an exemplary embodiment of the method, tasks are used, as in operant conditioning, but users are not trained to optimally perform the tasks. Pattern recognition is used to discover the pattern in the artifacts in the EEG signal that indicate the brain state the user is in while performing the task. The combination of operant conditioning and pattern recognition provides a way to detect brain states, the persistence of brain states, and transitions between brain states that may then be used to more directly measure the conditions of users such as, but not limited to, interruptability, cognitive workload, task engagement, communication mediation, interpreting and predicting system response, surprise, satisfaction, and frustration. Measures of the conditions may then be used to evaluate the effectiveness of systems and interfaces.

Embodiments of the method require only a small number of sensors, e.g., four, that can be placed fairly randomly and allow users to move. Using both cognitive and non-cognitive artifacts works well for assessing user interface effectiveness because the artifacts correlate well with the tasks that are being studied. Moreover, embodiments of the method do not require users to understand the system or control all or part of the system. Users are only required to perform the assigned tasks. The system more directly measures factors having to do with user interface effectiveness.

Figure 1:
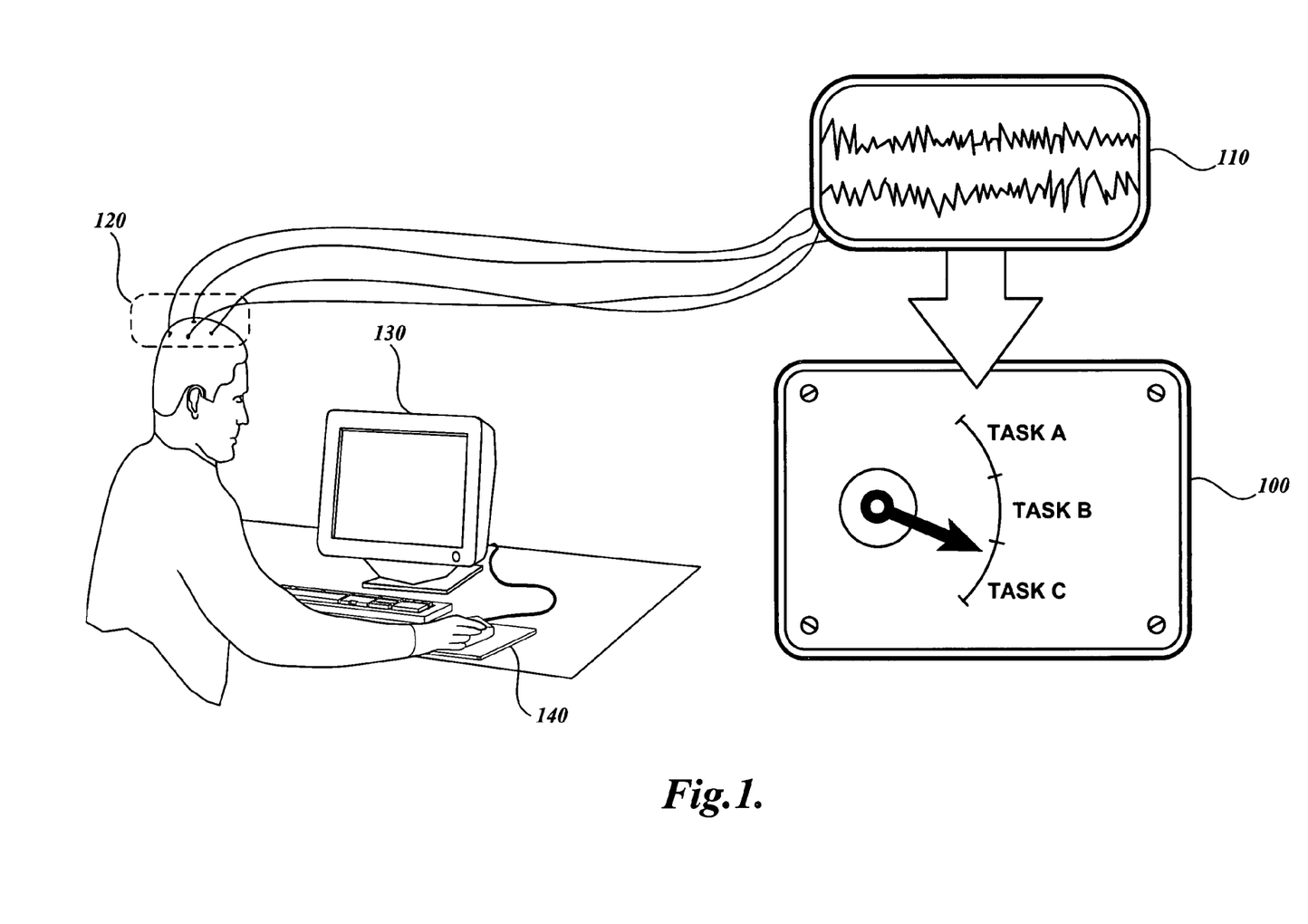
FIG. 1 is an illustration of an exemplary brain-computer interface using EEG signals for task classification.

The method uses a brain activity analysis system, i.e., a system, such as the exemplary system illustrated in FIG. 1. The exemplary system illustrated in FIG. 1 comprises a computing device 100 containing one or more software programs for analyzing EEG signals; an electronic device for recording sensor signals, e.g., an EEG 110; a sensor array 120; an electronic display 130; and a mouse 140. The sensor array 120 comprises two sensor pairs, i.e., four sensors, each of which is attached to a user's scalp. It is possible to use other electronic devices capable of recording sensor signals. The use of an EEG 110 should be considered exemplary and not limiting. Other input and output devices may be used in the system. Hence, the mouse 140 and the electronic display 130 should be construed as exemplary and not limiting. Input and output devices such as a mouse 140 and an electronic display 130 may be connected to, and communicate with, a computing device. The computing device to which the input and output devices are connected, e.g., a mouse 140 and an electronic display 130, may or may not be a computing device containing one or more software programs for analyzing EEG signals, e.g., computing device 100.

In the exemplary system illustrated in FIG. 1, a user performs a task using the mouse 140. The user views results of the task on the electronic display 130. Sensor pairs in the sensor array 120 sense electrical signals transmitted from a user's scalp. Electrical signals from the sensor pairs in the sensor array 120 are transmitted to the EEG 110. The EEG filters and transmits the electrical signals, i.e., EEG signals, to the computing device 100. The analysis software on the computing device 100 analyzes the EEG signals to determine the brain states associated with the task the user is performing.

Figure 2A:
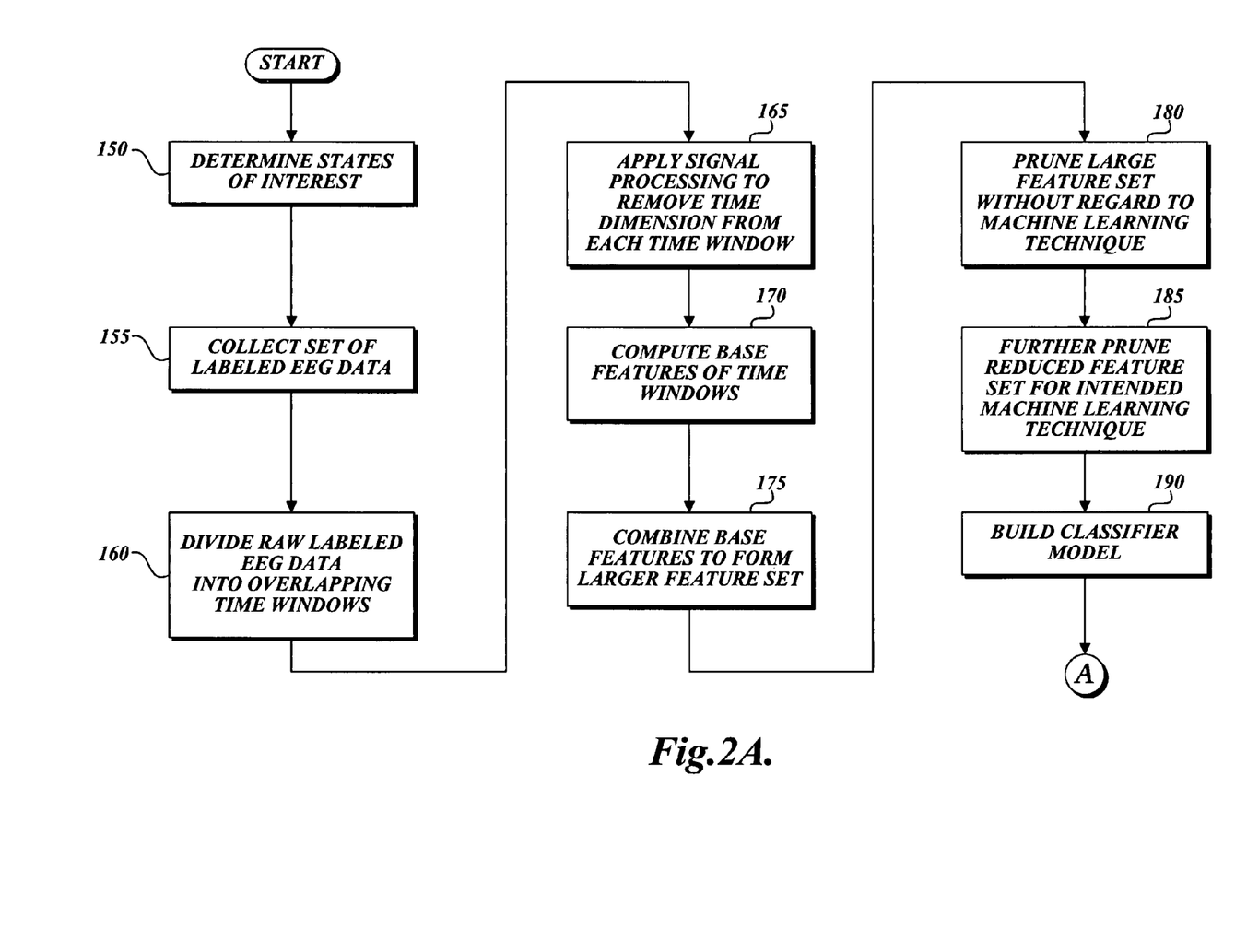
FIGS. 2A and 2B comprise a functional flow diagram illustrating an exemplary method of determining the effectiveness of a user interface using cognitive techniques.
Figure 2B:
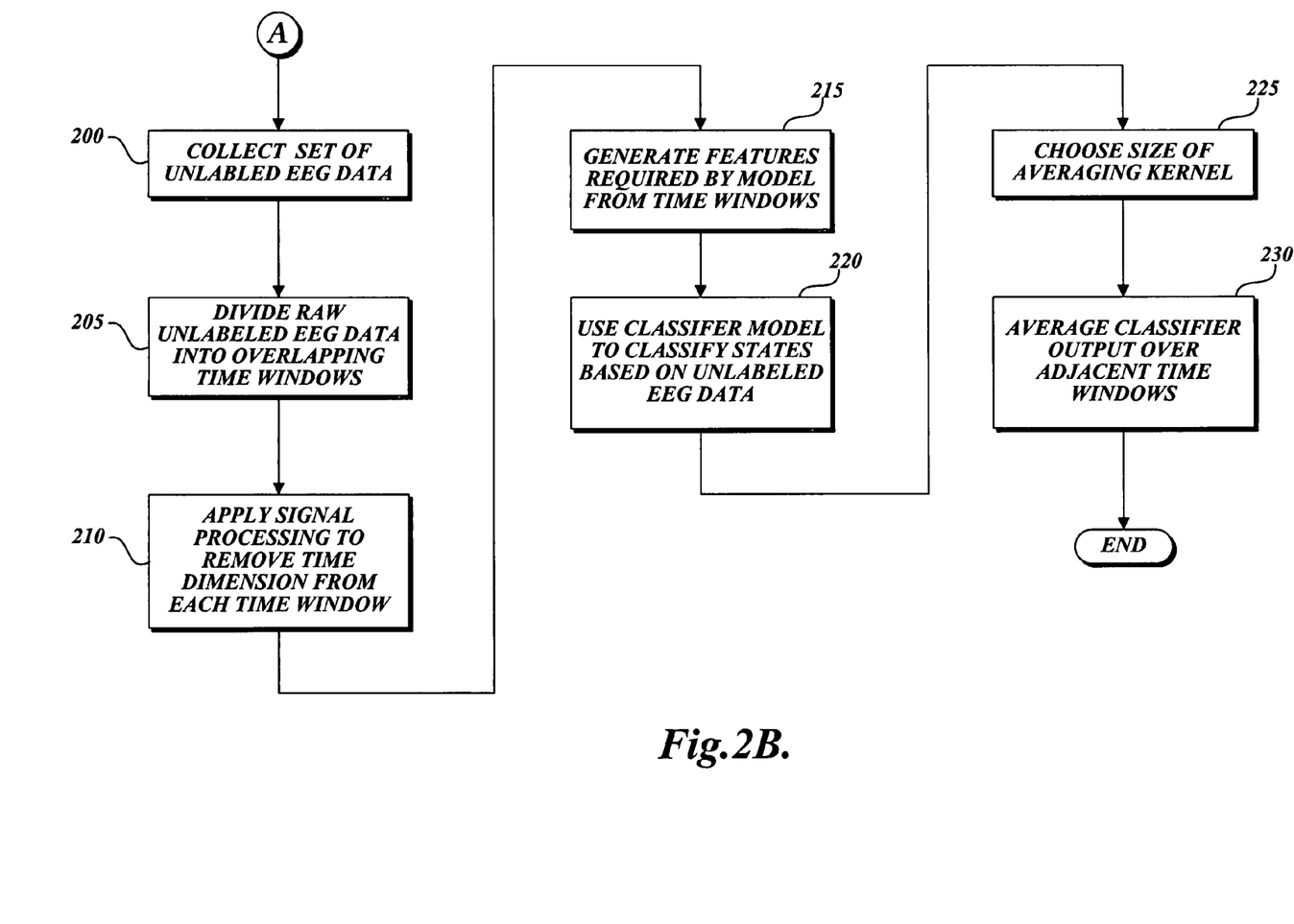

The exemplary system illustrated in FIG. 1 and described above may be used in methods for determining user interface effectiveness. FIGS. 2A and 2B comprise a functional flow diagram illustrating the two stages of an exemplary method for determining user interface effectiveness that blends elements of operant conditioning and pattern recognition and uses both cognitive and non-cognitive artifacts. The two stages of the method are: using labeled EEG data to build a classifier model, illustrated in FIG. 2A; and using the classifier model to classify brain states in unlabeled EEG data, illustrated in FIG. 2B. The exemplary method operates within a system such as the system illustrated in FIG. 1.

The exemplary method begins in FIG. 2A at block 150. At block 150, brain states of interest are determined. The number and nature of the brain states that are to be the focus of test sessions are selected. Exemplary brain states are brain states that may exist during tasks such as high and low workload, math calculations, 3D image rotation, playing a computer game, etc. For example, three brain states are determined. Each of the three brain states is associated with three mental tasks: rest, math calculation, and image rotation. A user is asked to rest, i.e., sit still without thinking about anything in particular. The user is then asked calculate the product of a pair of numbers, such as 34×257. The user is then asked to imagine some object, such as a peacock, rotated in 3D space. At block 155, a labeled set of the EEG data is collected. As the user performs the three tasks, the signals from a sensor array 120 are recorded by an EEG 110 and sent to a computing device 100. The unprocessed, i.e., raw, EEG data is "labeled" as having been collected during one of the three tasks and hence, may represent a brain state associated with a task.

The raw EEG data is time sequenced data. A single number representing the voltage difference between two sensors is generated at a time recording point. Voltage differences are sampled at some predetermined rate, such as 64 samples a second, yielding time sequenced data which may be used to chart voltage differences across time. Other sampling rates, such as 128 samples per second, are possible. Hence, the sampling rate of 64 samples per second should be construed as exemplary and not limiting. It is necessary to remove the time dimension from the time sequenced data because a machine learning technique is used later in the method and most machine learning techniques are unable to operate on data with a time dimension.

Figure 3:
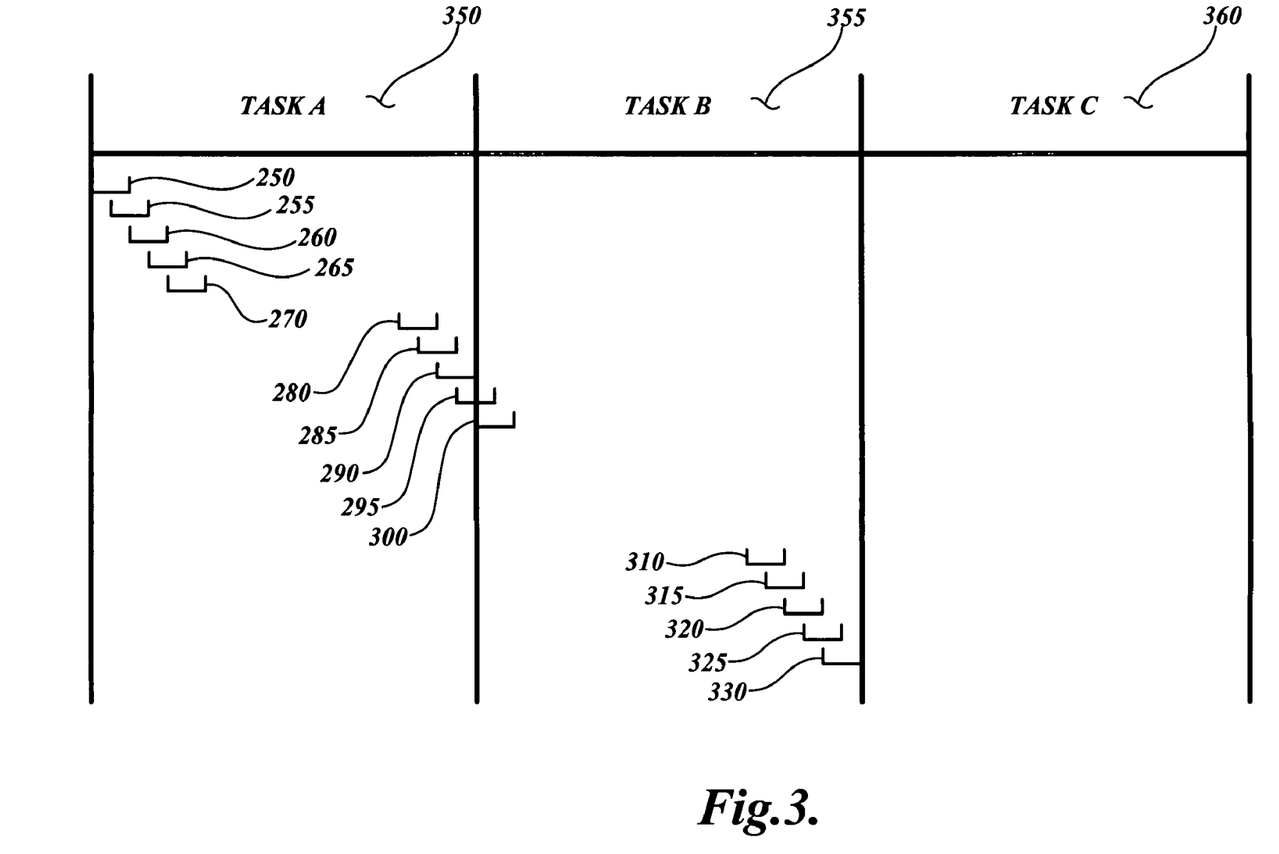
FIG. 3 is an exemplary chart illustrating three exemplary sets of time windows in three exemplary tasks.

The time dimension is removed by first dividing the data into time windows and then removing the time dimension from each of the time windows. Hence, at block 160, the raw labeled EEG data, i.e., time sequenced data, is divided into overlapping time windows such as the overlapping time windows illustrated in FIG. 3. Three exemplary sets of overlapping time windows placed in three exemplary "task periods" are illustrated in FIG. 3. A task period is the time period during which a task is performed and the data for the task is recorded. The task periods are Task A 350, Task B 355, and Task C 360. Time windows 250, 255, 260, 265, and 270 are placed at the beginning of Task A. Time windows 280, 285, 290, 295, and 300 are placed on the border between Task A and Task B. Time windows 310, 315, 320, 325, and 330 are placed within Task B. The right side of time window 330 touches the borderline between Task B and Task C. An exemplary size for a time window of an EEG data set is two seconds with a one second overlap. For example, the time windows illustrated in FIG. 3 may be two seconds long and overlap by one second. In particular, time window 250 may be two seconds long and overlap time window 255, which is also two seconds long, by one second. The last second in time window 250 is the first second in time window 255; the last second in time window 255 is the first second in time window 260, and so on. Other time window lengths and overlaps are possible, e.g., four seconds with a one second overlap. Thus, a two second long time window with a one second overlap should be considered exemplary and not limiting. Each time window can be considered a data "bin" in that each time window contains contiguous time dependent data.

In an exemplary test session, the raw labeled EEG data comprises 180 seconds of 2-channel 8-bit raw labeled EEG data for each task and each user. The first four seconds of raw labeled EEG data is removed from each task to be sure that data is collected only when the user is performing the task, e.g., the remaining 10 seconds of the task. Dividing each 10 second task into two second windows overlapping by one second provides nine windows per task period and a total of 486 windows for each user. A window is a set of overlapping task periods.

Returning to FIG. 2A, at block 165, signal processing techniques, e.g., performing Fourier transformations on the data in each time window, are applied to remove the time dimension from each time window yielding the spectral power in each time window. The spectral power is divided into a predetermined number of frequency bands, preferably six frequency bands. The preferred frequency bands are: 1-4 Hz, the delta band; 4-8 Hz, the theta band; 8-12 Hz the alpha band; 12-20 Hz the beta-low band; 20-30 Hz, the beta-high band; and 30-50 Hz, the gamma band. Those skilled in the art will appreciate that these frequency bands correspond to known types of neural activity. However, these bands should be construed as exemplary and not limiting. By performing Fourier transformations on the data in each time window, each time window contains a frequency spectrum that is no longer time dependent.

At block 170, the base features of the time windows are computed. The goal is to generate a large number of features from each of the time windows. Each time window is treated as generic data, i.e., as though the data contained no neurological properties. An exemplary number of features is 39. Exemplary features include, but are not limited to: the total power in each of the aforementioned six frequency bands for each channel; phase coherence in each band across channels; the difference in each band power between channels; mean spectral power; peak frequency; peak frequency magnitude; mean phase angle; mean value; zero-crossing rate; number of samples above zero; and mean spectral power difference between two input channels. There are a wide range of features that may be extracted from the data in the time windows. The number and types of features described herein should be construed as exemplary and not limiting.

At block 175, the base features, which were computed at block 170, are combined to form a larger feature set, i.e., data feature set. By mathematically combining the base features in various ways, it is possible to discover new features that may be substantially more predictive than the base features alone. Those skilled in the art will appreciate that mathematical manipulations of input features, e.g., the base features, are often used to compensate for a lack of expressiveness in the statistical models used by machine learning algorithms, such as the machine learning algorithms used later in the method. For example, computing the product and quotient between each pair of the 39 exemplary base features results in 1,482 additional features for a total of 1,521 features. Mathematically, the manipulations transforms a linear space and increase the size of the space by an order of magnitude thus curving the space and, in effect, creating a much larger space.

In addition to the multiplication and division of pairs of base features, there are a wide range of mathematical manipulations that may be applied to the set of base features. Other mathematical operations may be applied to the pairs. Operations may be performed on more than two features at a time. For example, we might multiply or divide sets of 3 features to create new ones. Hence, multiplying and dividing pairs of the base features to generate a larger feature set should be construed as exemplary and not limiting.

At block 180, the large feature set, i.e., the set of 1,521 features, is pruned without regard to machine learning technique. In the pruning process, features are selected according to how useful each feature is to the classification of the data. The less useful features are removed leaving a smaller set of more useful features. In particular, for the brain states determined at block 150, features are selected that provide the most information for classifying the brain states without overlapping with other features. The pruning is first done without regard for a particular machine learning technique because pruning requires a significant amount of compute time. Pruning for a particular learning technique substantially increases the compute time, often to an impractical level. Similarly, a smaller feature set is preferred to keep the amount of computing required later to a manageable level.

A way to prune the larger feature set without regard for a particular machine learning technique is to use a correlation-based filter which compares the information gain from each feature as well as the correlation between the features. The algorithm on which the correlation-based filter is based evaluates subsets of features favoring those that have a high correlation with the output variable while having a low correlation among the features with the selected set. For example, pruning the exemplary set of 1,521 features yields an average of 51 features for 3-task classifiers and an average of 39.2 features for models that discriminate between pairs of tasks. Thus, the feature set may be reduced to 50 features. There are other ways to prune a feature set, such as principal component analysis or using a wrapper based operator. Hence, the use of the correlation-based filter to prune a feature set should be construed as exemplary and not limiting.

At block 185, the reduced feature set is further pruned for the intended machine learning technique which is Bayesian networks. Other machine learning techniques, such as decision trees or SVMs may also be used. Hence, the use of Bayesian networks should be construed as exemplary and not limiting. Considering a machine learning technique when selecting features is computationally expensive which is why the less computationally expensive pruning, described above, is done. In further pruning the feature set, features are selected according to how useful each feature is to the classification of the data when using Bayesian networks to do the classification. In a feature set, certain features are better than other features to optimally train a Bayesian network to classify the data. For example, it may be that five features are available to predict that a person will live past the age of 70: age, current health, place of residence, education, and exercise habits. It may also be that if a Bayesian network is used to classify data, the features that optimally train the Bayesian network to classify the data are age and education. Hence, age and education are selected from the feature set, i.e., the remaining features are pruned.

To discover which of the 50 features selected by the correlation-based filter may be used to optimally train the Bayesian network, permutations of the 50 features are used to train the Bayesian network. For example, the 50 features are divided into two groups of 25 features. The first group is used to train the Bayesian network. The accuracy of the results of the classification by the Bayesian network using the first group of features is recorded. The second group is used to train the Bayesian network. The accuracy of the results of the classification by the Bayesian network using the second group is compared to the accuracy of the results of the classification using the first group. The features in the group producing more accurate results receive a higher "score" than the less accurate group. Using a similar strategy and beginning with an empty set of features, various permutations are performed and compared to build a classifier model by incrementally adding or removing features based on the features' impact on overall classification accuracy. Incrementally building a classifier model using the various permutations of the 50 features preferably reduces the number of features to an average of 23 features for the 3-task classifiers which have 486 example windows and an average of 16.4 features for the classifiers for two tasks which have 324 windows. Most of the processing time and effort is spent in the refined feature selection step just described.

Figure 4:
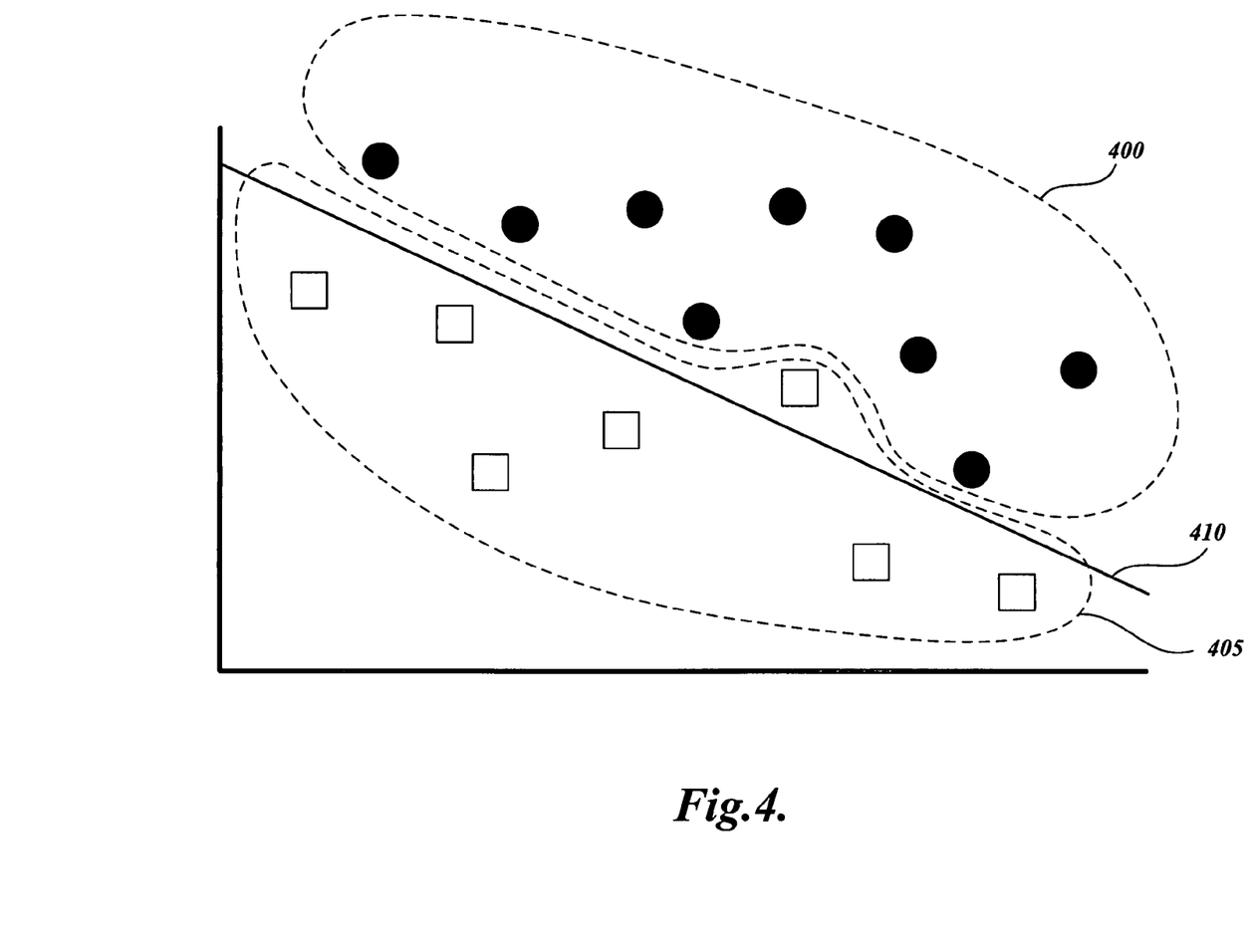
FIG. 4 is an exemplary chart illustrating a straight line dividing a data set into two classifications.
Figure 5:
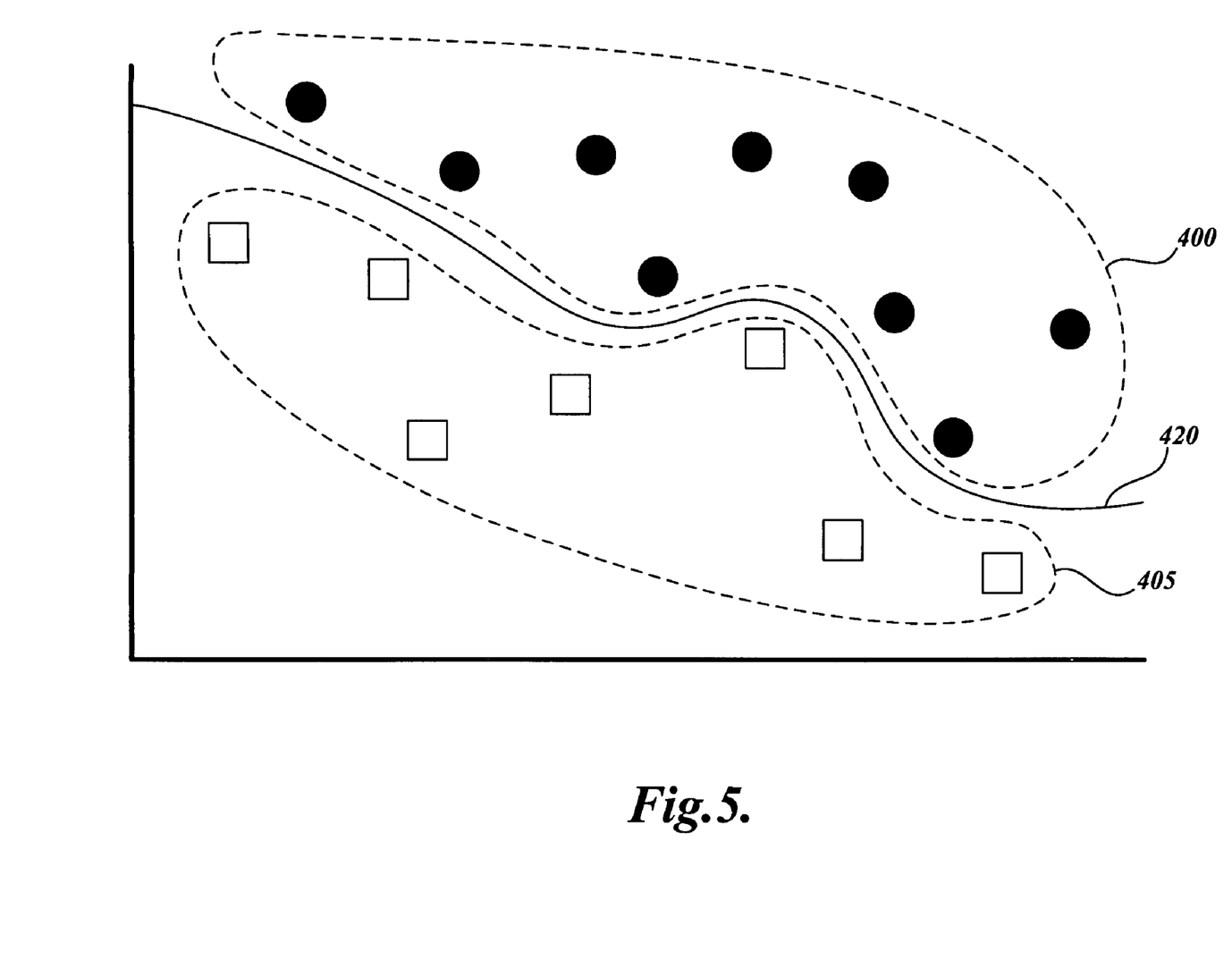
FIG. 5 is an exemplary chart illustrating a smoothly curved line dividing a data set into two classifications.
Figure 6:
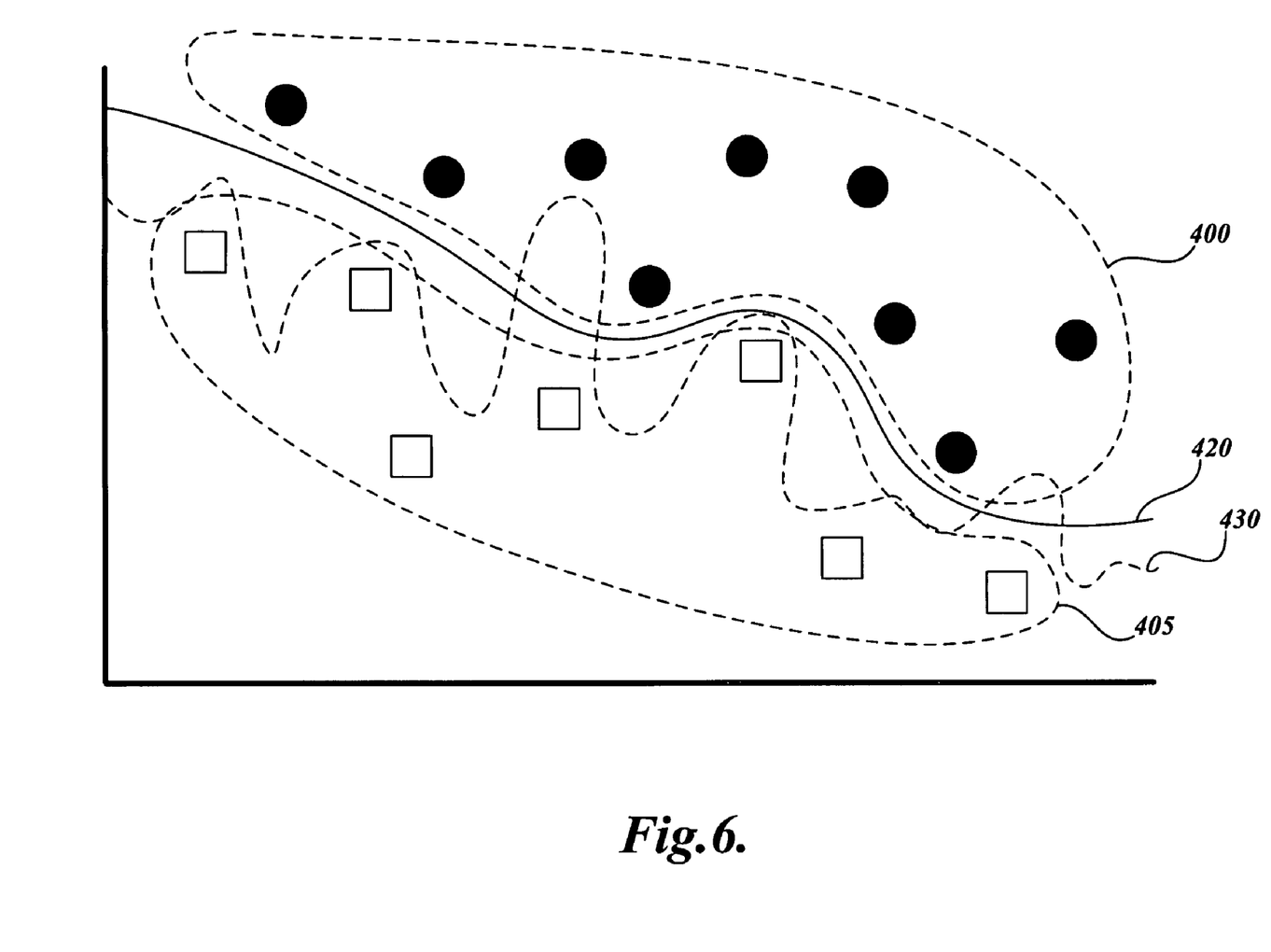
FIG. 6 is an exemplary chart illustrating an overfitted curved line, dividing a data set into two classifications.

At block 190, a classifier model is built. The final steps of incrementally building a classifier model are completed resulting in a machine learning model and a set of features. The Bayesian net is trained using a set of known test data. The test data is divided into various combinations of the features. The trained Bayesian net enables the classification of unlabeled data. The concept of classifying unlabeled data is illustrated in FIGS. 4-6. FIG. 4 illustrates two data sets indicating two brain states. Data set 400 comprises a group of nine black dots that may represent, for example, nine instances of a feature associated with a brain state during which a user is performing a math calculation. Data set 405 comprises a group of eight white squares that may represent, for example, eight instances of a feature associated with the user's rest brain state. A straight line 410 runs from the upper left to the lower right corner roughly separating the two data sets, i.e., separating the dots from the squares. The straight line 410 represents a classifier, for example, a Bayesian net that is in "early training." Because one of the white squares in data set 405 is above the straight line 410, the classifier, i.e., the Bayesian net, is not as accurate as it could be. With further training, the classifier may look more like the curved line 420 in FIG. 5.

In FIG. 5, data set 400 is cleanly separated from data set 405 by the curved line 420. All of the black dots in data set 400 are above curved line 420 and all of the white squares in data set 405 are below curved line 420. Curved line 420 represents a good classifier, i.e., a classifier that adequately separates the data indicating one brain state, e.g., math calculation, from the date indicating a different brain state, e.g., rest. Typically, in machine learning, there are data points in a space and the classifier attempts to draw a line, e.g., straight line 410, through the space to classify the data, i.e., data above the straight line 410 versus the data below the straight line 410. By using mathematical manipulations, e.g., taking the products and quotients of data pairs, the space is warped so the line, e.g., curved line 420 "wiggles" through the data. This produces a more complex and effective classification, i.e., more of the appropriate data is classified. In the quest for effective classification, various quantities of data may be used to form combinations. For example, two, three, four, or more data points may be used to form combinations. The combinations may involve a variety of mathematical functions such as, but not limited to, multiplication, division, log functions, etc. What limits the choice of the number of data points in the combinations and the mathematical functions used to combine the points is mathematical complexity and overfitting.

An increase in mathematical complexity increases the likelihood of inaccuracies and increases computing time.

Overfitting can be loosely described as combining too many of the features in too many ways and/or in ways that are too complicated such that the line, i.e., classifier, becomes "too squiggly" as illustrated in FIG. 6. FIG. 6 illustrates the same data sets, i.e., data sets 400 and 405, that were illustrated in FIGS. 4 and 5. The curved line 420 that cleanly separates the data sets shown in FIG. 5 is also shown in FIG. 6. The "too squiggly", i.e., overfitted, curved line 430 shown in FIG. 6 represents an overfitted classifier. It can be seen in FIG. 6 that although the overfitted curved line 430 separates the two data sets 400 and 405, the excessive curves in the overfitted curved line 430 make it less likely to separate other similar data sets. The classifier that overfitted curved line 430 represents has less generality than the classifier represented by curved line 420. Having less generality means that it is more difficult to infer knowledge from the data. Hence, it is preferable to reduce the possibility of overfitting. Reducing overfitting may be accomplished by using a smaller feature set, reducing the number of data points in the combinations, and/or reducing the complexity of the mathematical functions used to combine the points.

After a classifier model is built, the method continues into the second stage, i.e., using the classifier model to classify brain states in unlabeled EEG data, as illustrated in FIG. 2B. The second stage begins at block 200 in which an unlabeled set of EEG data is collected. The EEG data that is collected is not associated with a known brain state. At block 205, the raw unlabeled EEG data is divided into overlapping time windows, similarly to the way labeled EEG was divided into overlapping time windows in block 160 shown in FIG. 2A. At block 210, signal processing is applied to the overlapping time windows to remove the time dimension from each time window, similarly to the way signal processing is applied to the overlapping time windows in block 165 shown in FIG. 2A.

At block 215, the features required by the model are generated from the time windows. At block 220, the user classifier model is used to classify brain states based on the unlabeled EEG data. To increase the accuracy of determining brain states, preferably, the results are averaged over time. In the exemplary method described herein, the EEG signal was sliced into overlapping two second windows. The classifier takes the features from each two second window and classifies feature as being from, for example, the math calculation brain state or the rest brain state. The classifier determines if, during that two second period, the user performing a math calculation or was at rest. With tasks that last more than two seconds, by averaging over groups of the two second windows, the accuracy of determining when a user is in a particular brain state goes up. In a sense, averaging provides a confidence voting scheme in which the most likely brain state is "voted in." Reintroducing the temporal nature of the data by averaging the classifier output over several adjacent time windows reduces the impact of spurious artifacts thereby substantially improving the overall classification accuracy. To perform the averaging over time, at block 225, the size of the averaging kernel is chosen, i.e., the number of time windows to average is chosen, in order to produce the final classifier output. At block 230, the classifier output is averaged over time of the adjacent time windows. After block 230 the process ends.

In scenarios where the classifier has no knowledge of when a task begins and ends, the best strategy may be to choose a fixed kernel size, e.g., for each classifier output, average the raw classifier output over five time windows. If all five time windows come from the same task, e.g., time windows 250, 255, 260, 265, and 270, averaging reduces the impact of noise in the windows and the final output is more likely to be correct. If all five windows do not come from the same task, i.e., the five windows include a transition between tasks, e.g., time windows 280, 285, 290, 295, and 300, the averaging kernel contains conflicting information and the classification accuracy will be poor around these data points. Thus, the benefit of averaging the classifier output depends on the density of task transitions in the EEG data. More precisely, the impact that averaging over time has on overall classification accuracy is directly related to the ratio between the kernel size and the expected duration of the tasks.

Figure 7:
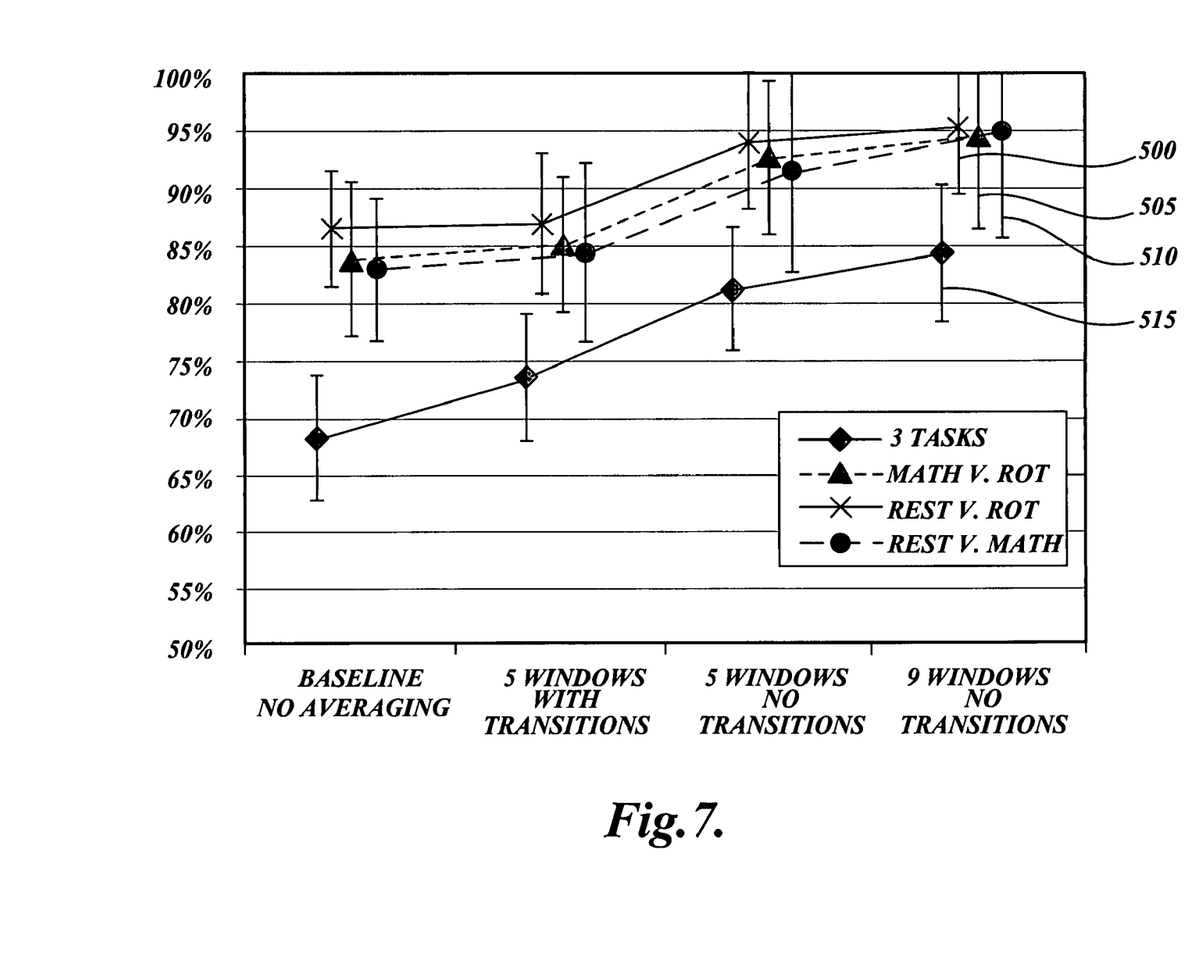
FIG. 7 is an exemplary chart plotting the overall classification accuracies for three mental tasks under various averaging scenarios.
Figure 8:
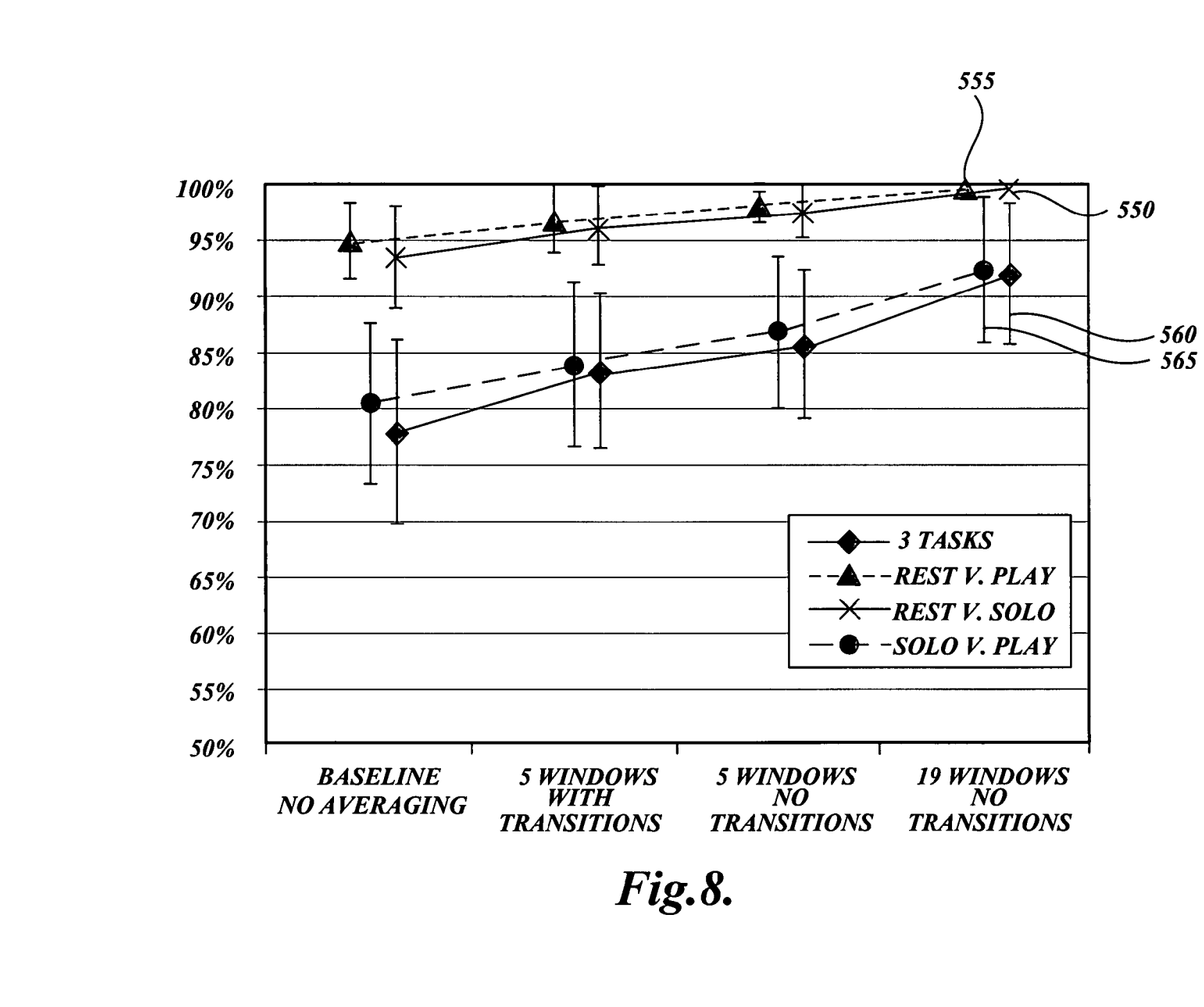
FIG. 8 is an exemplary chart plotting the overall classification accuracies for three game tasks under various averaging scenarios.

Exemplary charts illustrating the effect of the ratio between the kernel size and the expected duration of the tasks on overall classification accuracy are shown in FIGS. 7 and 8. The FIG. 7 exemplary chart illustrates the mean classification accuracy for three mental tasks in four averaging scenarios. The four averaging scenarios are listed on the chart's horizontal axis: Baseline No Averaging; 5 Windows with Transitions; 5 Windows No Transitions; and 9 Windows No Transitions. The chart's vertical axis indicates the classification accuracy of the three mental tasks as a percentage with 100% indicating that the classification of a brain state matched the duration of a task. The percentages on the vertical axis range from 50% to 100% in 5% increments. Four curves are plotted on the exemplary chart shown in FIG. 7. Each curve contains four data points with each data point having an error bar representing standard deviation. Curve 500 represents the results of distinguishing the transitions between the Rest and the Rotation tasks. Curve 505 represents the results of distinguishing the transitions between the Math and the Rotation tasks. Curve 510 represents the results of distinguishing the transitions between the Rest and the Math tasks. Curve 515 represents the results for a 3-task classifier.

The Baseline No Averaging scenario shows the baseline accuracy of raw classifier output with no averaging and is the control scenario to which the results in the remaining three scenarios are compared. In the 5 Windows with Transitions scenario, the duration of each task is not significantly longer than the kernel size. The kernel size is five. Each time is two seconds wide. The windows in a kernel requires six seconds of data. The tasks last 10 seconds each resulting in 40% of the classifications being averaged over conflicting data, i.e., data from two tasks resulting in poor classification. If the task durations are significantly longer than the kernel size, the amount of conflicting data is reduced. Having task durations significantly longer than the kernel size is simulated in the 5 Windows No Transitions scenario by using the data from the 5 Windows with Transitions scenario but leaving out data sets that span transitions. In the 9 Windows No Transitions scenario the kernel size is nine which requires 10 seconds of data and allows the kernel to span the 10 second task duration. In essence, these allows a classifier to sense the beginnings and ends of tasks. It can be seen that classification accuracy improves with each scenario shown in FIG. 7.

Similarly, it can be seen that classification accuracy improves with each scenario shown in FIG. 8 which illustrates the mean classification accuracy for three game tasks in four averaging scenarios. The game tasks are performed using a computer or video game, e.g., Halo. Games such as Halo are referred to as "first person shooters" because the user hunts and shoots at targets in the game requiring the user to almost constantly operate the game controls. Hence, such game tasks involve more physical movement and so provide a more realistic example of using the method. The four averaging scenarios are listed on the chart's horizontal axis: Baseline No Averaging; 5 Windows with Transitions; 5 Windows No Transitions; and 19 Windows No Transitions. The chart's vertical axis indicates the classification accuracy of the three mental tasks as a percentage with 100% indicating that the classification of a brain state matched the duration of a task. The percentages on the vertical axis range from 50% to 100% in 5% increments. Four curves are plotted on the exemplary chart shown in FIG. 8. Each curve contains four data points with each data point having an error bar representing standard deviation. Curve 550 represents the results of distinguishing the transitions between the Rest and the Solo tasks. Curve 555 represents the results of distinguishing the transitions between the Rest and the Play tasks. Curve 560 represents the results for a 3-task classifier. Curve 565 represents the results of distinguishing the transitions between the Solo and the Play tasks.

Note that embodiments of the method described above and illustrated in FIGS. 2A-2B are not concerned with replacing physical input. Because replacing physical input is not a concern, the users from which the EEG signals are collected may be neurologically healthy individuals as opposed to brain-damaged or physically damaged individuals. Embodiments of the method can operate in real world settings that do not rely on tightly controlled settings, e.g., having users close their eyes, restraining users, insulating the test area from electromagnetic radiation, etc. As described above, traditionally, sensors are placed in standard patterns. Embodiments of the method are likely to be successful regardless of where on the scalp the sensors are placed because the voltages measured are not tightly associated with specific neurological phenomena.

The exemplary process, i.e., exemplary method, illustrated in FIGS. 1-8 and described above provides a more direct way to determine the effectiveness of user interfaces. A central characteristic of the method, i.e., using artifacts, is also an advantage. Whereas other cognitive neuroscience techniques expend much time and effort on eliminating or damping artifacts, the method described above treats artifacts as useful data. This is akin to producing a new, useful material from what was considered waste products.

Another advantage of the method is the ability to use low cost, low precision devices to perform relatively sophisticated studies. For example, an inexpensive, e.g., $1,500, EEG may be used in the method as compared to the expensive, e.g., $20,000-$200,000, EEGs used for other cognitive neuroscience techniques. The equipment used to carry out the method may be off-the-shelf and easy to find.

Yet another advantage of the method is the ability to use a low number of channels, e.g., two channels comprising two pairs of sensors. The four sensors can be placed on the user in many configurations as long as a configuration yields voltage differences between the sensors. Typically, in other EEG applications at least eight channels, i.e., sixteen sensors, are required. Besides requiring additional sensors, other EEG applications require that the sensors be arranged on the user's scalp in predetermined, tightly controlled patterns.

While the exemplary method is described above in the context of determining user interface effectiveness, the method may be used to evaluate the cognitive utility of user interfaces. For example, the method may be used to determine the cognitive workload levels, or workload types, e.g. verbal vs. spatial, of a plurality of user interfaces to compare the user interfaces' cognitive utility. It may also be possible to use the method to evaluate user interface cognitive utility and redesign user interfaces in, real time to dynamically adapt user interfaces to users' states. Examples of such real time user interface adaptation include, but are not limited to, determining optimal information presentation, managing interruptions, adjusting the level of detail in displays, adapting user interface controls and layouts, adapting multimodal data presentation schemes, etc. For example, if a user is cognitively overloaded, i.e., has no more cognitive resources to deal with new information, the method may enable a system to recognize pending interruptions so that the system can buffer the interruptions until a user is less cognitively loaded. Alternatively, the method may enable a system to recognize that a user is verbally overloaded and present information in a spatial manner to use a user's spatial cognitive resources. The method may also be used to present an enhanced, detailed awareness of pluralities of users enabling systems to dynamically distribute tasks among groups of users working on a common task.

While illustrative embodiments have been illustrated and described, it will be appreciated that various changes can be made therein without departing from the spirit and scope of the invention. For example, classifiers are trained on specific sets of tasks performed specific users. It is possible that not all artifacts used by the classifiers vary from user to user. It may be that certain artifacts might be generalizable. It is also possible that the information output by the method can be used as input that can be fed back into a system, e.g., a user interface, to inform the system how to adapt to help the user perform tasks.

The embodiments of the invention in which an exclusive property or privilege is claimed are defined as follows:

1. A method for classifying brain states comprising obtaining from at least one electroencephalograph (EEG) sensor labeled EEG data signals that include artifacts, building a classifier model with at least one computer device using the labeled EEG data signals that include artifacts and using the classifier model to classify brain states in unlabeled EEG data signals without at any point requiring the removal of the artifacts from the EEG data signals, wherein building a classifier model with the least one computer device comprises:
   a) determining brain states of interest;
   b) collecting a set of labeled EEG data signals that include artifacts;
   c) dividing the labeled EEG data into overlapping time windows;
   d) removing the time dimension from each time window;
   e) generating features from the time windows; and
   f) building the classifier model.

2. The method of claim 1, wherein generating features from the time windows comprises;
   a) computing the base features of the time windows;
   b) combining the base features to form a larger feature set;
   c) pruning the larger feature set without regard to machine learning techniques; and
   d) further pruning the feature set for a machine learning technique.

3. The method of claim 1, wherein classifying brain states using the classifier model comprises:
   a) collecting a set of unlabeled EEG data signals that include artifacts;
   b) dividing the unlabeled EEG data into overlapping time windows;
   c) removing the time dimension from each time window;
   d) generating features required by the classifier model from the time windows;
   e) using the classifier model to classify brain states in the unlabeled EEG data;
   f) choosing the size of the averaging kernels; and
   g) averaging the classifier output over adjacent time windows.

4. The method of claim 1, wherein the artifacts included in the labeled EEG data signals includes cognitive artifacts.

5. The method of claim 1, wherein the artifacts included in the labeled EEG data signals includes cognitive and non-cognitive artifacts.

6. The method of claim 1, wherein the artifacts included in the unlabeled EEG data signals includes cognitive artifacts.

7. The method of claim 1, wherein the artifacts included in the unlabeled EEG data signals includes cognitive and non-cognitive artifacts.

8. The method of claim 1, wherein the EEG signals are collected from pairs of sensors attached to individuals.

9. The method of claim 8, wherein individuals are neurologically healthy individuals.

10. The method of claim 9, wherein the neurologically healthy individuals are users in tests to evaluate user interfaces.

11. The method of claim 1, wherein the pairs of sensors comprise two pairs of sensors.

12. The method of claim 1, wherein the brain states are associated with at least one condition of users selected from the group of user conditions comprising:
 interruptability, cognitive workload, task engagement, communication mediation, interpreting and predicting system response, surprise, satisfaction, and frustration.

13. The method of claim 1, including discriminating at least two different brain states.

14. The method of claim 1, including determining the persistence of brain states.

15. The method of claim 1, including determining the transitions between brain states.

16. The method of claim 1, wherein a plurality of features is generated and then pruned.

* * * * *